United States Patent
Grundei et al.

(10) Patent No.: US 6,793,680 B2
(45) Date of Patent: Sep. 21, 2004

(54) KNEE JOINT ENDOPROSTHESIS

(75) Inventors: Hans Grundei, Lübeck (DE); Wolfram Thomas, Rome (IT)

(73) Assignee: ESKA Implants GmbH & Co., Lübeck (DE)

( * ) Notice: Subject to any disclaimer, the term of this patent is extended or adjusted under 35 U.S.C. 154(b) by 0 days.

(21) Appl. No.: 10/463,267

(22) Filed: Jun. 17, 2003

(65) Prior Publication Data

US 2004/0024467 A1 Feb. 5, 2004

Related U.S. Application Data

(63) Continuation of application No. PCT/EP01/14968, filed on Dec. 18, 2001.

(30) Foreign Application Priority Data

Dec. 20, 2000 (DE) .......................................... 100 65 940

(51) Int. Cl.$^7$ ................................................. A61F 2/38
(52) U.S. Cl. .................................................... 623/20.31
(58) Field of Search ........................... 623/20.14, 20.21, 623/20.24, 20.28, 20.29, 20.31, 20.33

(56) References Cited

U.S. PATENT DOCUMENTS

| 4,209,861 A | * | 7/1980 | Walker et al. | ............ 623/20.27 |
| 6,099,570 A | * | 8/2000 | Livet et al. | ............... 623/20.21 |
| 2003/0004577 A1 | * | 1/2003 | Running | ................... 623/20.27 |

FOREIGN PATENT DOCUMENTS

EP 0 864 306 A2 9/1998

* cited by examiner

*Primary Examiner*—Eduardo C. Robert
*Assistant Examiner*—Michael B. Priddy
(74) *Attorney, Agent, or Firm*—Akin Gump Strauss Hauer & Feld, L.L.P.

(57) ABSTRACT

A knee joint endoprosthesis is provided having a femoral part (1) that can be linked with a shank part to be anchored in the femur, the femoral part being provided with two runners (2, 3) interlinked ventrally via a bridge. A tibia plateau part (5) interacts with a shank part to be anchored in the tibia and is provided with two slide guides (6) in which the runners (2, 3) of the femoral part (1) can roll off and slide. With increasing bend of the knee joint and upon exceeding a predetermined bending angle, the femoral part is allowed to perform an increasing rotation relative to the tibia plateau part (5).

8 Claims, 1 Drawing Sheet

KNEE JOINT ENDOPROSTHESIS

CROSS-REFERENCE TO RELATED APPLICATIONS

This application is a continuation of International Application No. PCT/EP01/14968, filed Dec. 18, 2001, the disclosure of which is incorporated herein by reference.

BACKGROUND OF THE INVENTION

The present invention relates to a knee joint endoprosthesis, and particularly as a total replacement implant.

Knee joint endoprostheses of this type are known in many embodiments, and are already in clinical use. Fundamental efforts have been made to emulate the natural, anatomical sequence of motion in such an artificial joint, in order, for example, not to place an excessive strain on the system of ligaments, insofar as these remain intact.

Known anatomical knee joint endoprostheses usually include a femoral part connectable with a shank part that is to be anchored in the femur bone. This femoral part is provided with two runners (sliding parts), which are connected ventrally with one another via a bridge. There are also embodiments in which the runners are fashioned in one piece with the shank part. However, within the scope of the present invention it is not important whether the femoral part has a one-part or a multi-part construction.

In addition, an anatomical knee joint endoprosthesis usually includes a tibia plateau part which works together with a shank part that is to be anchored in the tibia bone. This tibia plateau part is preferably made of a plastic, such as high-density polyethylene, in which two slide guides are formed, on which the runners of the femoral part can execute a roll-off and sliding movement.

Corresponding to the pre-existing physiological conditions in such an anatomical knee joint—starting from the extended position of the joint—as the bending of the joint increases, the possibility becomes greater that the femoral part rotates around the tibia part. At the same time, the femoral part executes a drawer-like movement in the dorsal direction on the tibia plateau part.

Other designs do not take a purely anatomical approach, but instead attempt to meet the needs of the patient through a purely technological approach. Thus, for example in DE 100 60 850, which was not prior published, applicant has proposed a set for constructing a tibia part of an above-mentioned knee joint endoprosthesis, comprising a base (or pedestal) part as well as at least two plastic supports that can be seated loosely on the base part. The slide guides for the runners of a femoral part of the endoprosthesis are formed in these plastic supports. The slide guides of the second plastic support are displaced relative to those of the first plastic support from the ventral side toward the dorsal side by a distance that can be between 0 and 12 mm. With this set the condition of the patient's system of ligaments is in particular taken into account, and the surgeon will assemble from the set an implant tailored to the individual patient. As stated, this approach is purely technological, and offers a plausible alternative to anatomical knee joint endoprostheses.

The scientific discussion concerning the advantages and disadvantages of one solution or the other has not reached a final conclusion. For the respective patient under treatment, each approach has advantages and disadvantages in accordance with the indications of the case.

BRIEF SUMMARY OF THE INVENTION

Against this background it is now an object of the present invention to further develop a knee joint endoprosthesis of the type described at the outset, in such a manner that aspects of both the purely anatomical knee joint endoprosthesis and of the purely technological endoprosthesis are realized, in order to combine the respective advantages of both types of endoprosthesis in one.

This object is achieved by a knee joint endoprosthesis having:

a femoral part connectable with a femur shank part to be anchored in a femur bone, the femoral part being provided with two runners connected with one another ventrally via a bridge, and a tibia plateau part working together with a tibia shank part to be anchored in a tibia bone, in which tibia plateau part there are formed two slide guides on which the runners of the femoral part can execute a rolling-off and sliding movement, wherein the tibia plateau part is pivotably mounted on the tibia shank part by a rotation mechanism, a negative and positive fit between the femoral part and the tibia plateau part being produced up to a predetermined bending angle of the knee joint, such that a rotational movement of the femoral part on the tibia shank part can be executed due to the pivotable mounting of the tibia plateau part on the tibia shank part, and wherein the femoral part is enabled to execute an increasing rotation of the femoral part relative to the tibia plateau part as the bending of the knee joint increases starting from the predetermined bending angle, without activating the rotation mechanism between the tibia plateau part and the tibia shank part.

Advantageous further developments are set forth below and in the dependent claims.

It is fundamentally proposed that the tibia plateau part be pivotably mounted on the tibia shank part so as to be able to be pivoted by a rotation mechanism and, up to a predetermined bending angle of the knee joint, effect a force- and form-fit (negative and positive) connection between the femoral part and the tibia plateau part, such that the femoral part can execute a rotational movement on the tibia shank part in the tibia bone due to the pivotable mounting of the tibia plateau part on the tibia shank part. On the other hand, an increasing rotation of the femoral part relative to the tibia plateau part is enabled as the bending of the knee joint increases starting from the predetermined bending angle, without, however, activating the rotation mechanism between the tibia plateau part and the tibia shank part.

Starting from the extended position of the knee joint, as the knee first bends, the motion sequence of a technological knee joint is at first most evident. Here, before a particular bending angle has been exceeded, the negative and positive fit between the femoral part and the tibia plateau part catches hold, and the purely technologically conditioned possibility of rotational movement, due to the mounting of the tibia plateau part on the tibia shank part, permits the femoral part to execute a rotational movement relative to the tibia shank part by means of a rotation mechanism. Thus, until a certain bending angle has been exceeded, the femoral part carries the tibia plateau part along in its movements and executes, as a unit therewith, a rotational movement on the tibia shank part anchored to the tibia bone. Subsequently, upon exceeding the predetermined bending angle, a regular switching takes place inside the endoprosthesis, between the previous technologically conditioned sequence of motion and the purely anatomical sequence of motion that then comes to bear. For this reason, this joint is also designated a hybrid joint, because it unites the anatomical and the technological aspects of known endoprostheses.

In a concrete preferred embodiment, it is provided that the runners of the femoral part delimit between them an open space that runs from the ventral side to the dorsal side, and that the two slide guides of the tibia plateau part are separated by two webs running aligned from dorsal to ventral. Here, the dorsally situated web has a height such that, up to the predetermined bending angle of the knee joint, it engages in the open space between the runners of the femoral part, thus creating the negative and positive fit. The ventrally situated web, in contrast, has only such a height that, as the bending of the knee joint increases, beginning with the exiting of the dorsal web from the open space between the slide guides of the femoral part, i.e., after the switch between technologically conditioned movement and anatomical movement, an increasing rotation of the femoral part is enabled relative to the tibia plateau part, but without activation of the rotation mechanism. This means that the ventrally situated web has a very low height and primarily exercises a guide function.

In this specific embodiment, the "switching" is realized by the femoral part and by the tibia plateau part, in the one case by the open space between the runners having corresponding support surfaces, and in the other case by the formation of the dorsally situated web, whose side walls come into contact with the side edges of the condyles of the femoral part and transmit the flow of force.

In a further preferred development the predetermined bending angle for a tibia plateau part lies in a range of about 20° to about 40°, the negative and positive fit between the femoral part and the tibia plateau part being effective up to the point at which this angle is exceeded. The "switching" of the knee joint thus takes place in the indicated range of about 20° to about 40°. The actual termination of the negative and positive fit as the bending of the joint increases depends decisively on the height of the dorsally situated web of the tibia plateau part, and can be determined individually for each patient.

According to an advantageous further development, it is also possible for the ventrally situated web to transition into the dorsally situated web. From the point of view of manufacturing technology, this is a simplification.

According to an advantageous embodiment, the rotation mechanism between the tibia plateau part and the tibia shank part comprises a pin that is integrally formed on the tibia shank part and that points towards the femur, and a correspondingly dimensioned bore in the underside of the tibia plateau part, in which the pin engages. This type of pivotability of a tibia plateau part on the tibia shank part is known per se.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
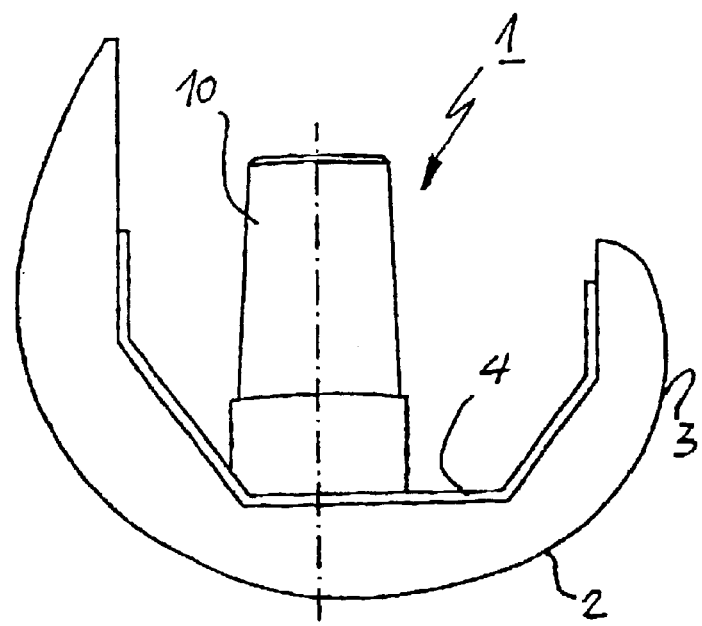
FIG. 1 is a schematic side view of a femoral part according to the invention.
Figure 2:
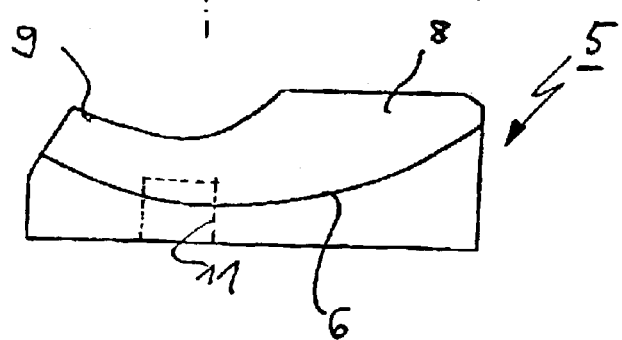
FIG. 2 is a schematic side view of a tibia plateau part according to the invention.

The femoral part 1 is shown schematically in FIG. 1. It has the two runners connected with one another ventrally, i.e., at left in FIG. 1, via a bridge (not shown). Runners 2 and 3 delimit between them an open space 4 that runs from the ventral side toward the dorsal side. A plugging cone 10 is provided here as a coupling element to a shank part to be anchored in the femur bone.

Runners 2 and 3 of femoral part 1 according to FIG. 1 slide and roll-off on slide guides 6 that are formed in tibia plateau part 5. Tibia plateau part 5 works together with a shank part (not shown) to be anchored in the tibia bone. Between tibia plateau part 5 and the corresponding tibia shank part a rotation mechanism is provided, that is known per se and that comprises essentially a pin integrally formed on the tibia shank part and pointing toward the femur, and that engages in a bore 11 in the underside of tibia plateau part 5.

Figure 3:
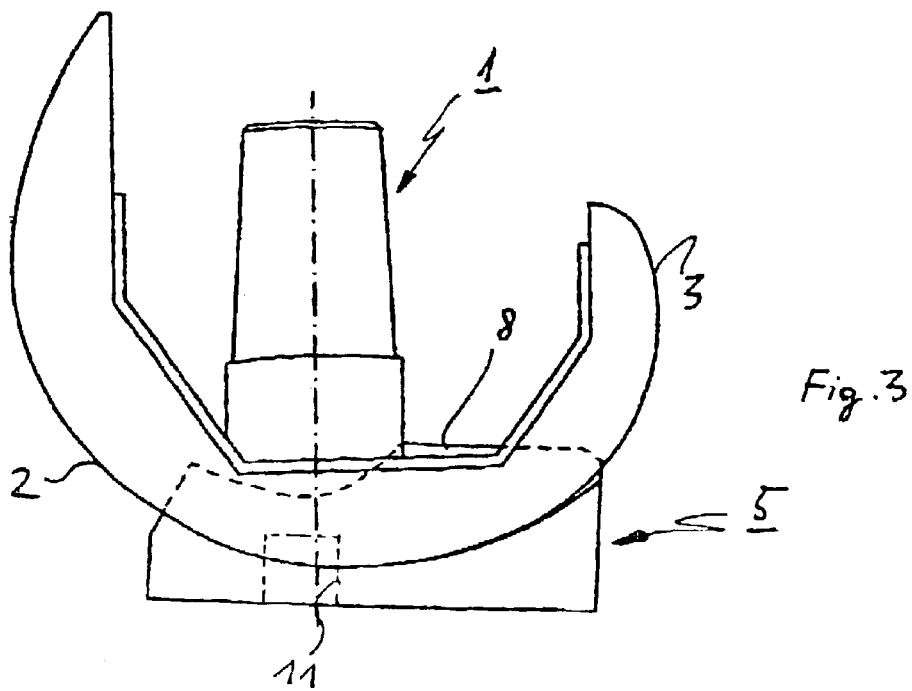
FIG. 3 shows the interplay of the femoral part and the tibia plateau part according to FIGS. 1 and 2.

The two slide guides 6 of tibia plateau part 5 are separated from one another by a ventrally situated web 9 and a dorsally situated web 8. Here, the ventrally situated web 9 transitions continuously into dorsally situated web 8. Dorsally situated web 8 has a significantly greater height than ventrally situated web 9. This serves the purpose that the dorsally situated web 8 acts as a mechanical switching element for the knee joint. As can be seen in FIG. 3, in which the femoral part 1 is depicted as seated on tibia plateau part 5 in the extended position of the knee joint, the dorsally situated, higher web 8 engages in the open space 4 between slide guides 2 and 3 of femoral part 1. In this way, a negative and positive fit is created between the two parts, and a possibility of rotation of femoral part 1 relative to the shank part in the tibia is thereby provided.

As the bending increases, the support surface of web 8 on the side edges of runners 2 and 3 becomes smaller, until web 8 moves out of engagement with open space 4. This is exactly the switching point between the technologically enabled movement sequence and the anatomical movement sequence. Upon exceeding a bending angle in a range of about 20' to about 40', the value of which can be determined for the individual patient by selecting an appropriate tibia plateau part 5, only the ventrally situated, lower web 9 assumes the guide function for slide guides 2 and 3. This creates a possibility of rotational movement for femoral part 1 relative to tibia plateau part 5, completely independently of the rotation mechanism between tibia plateau part 5 and the shank part in the tibia bone.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. Knee joint endoprosthesis, comprising a femoral part (1) connectable with a femur shank part to be anchored in a femur bone, the femoral part having two runners (2, 3) connected with one another ventrally via a bridge; and a tibia plateau part (5) working together with a tibia shank part to be anchored in a tibia bone, the tibia plateau part (5) having formed therein two slide guides (6) on which the runners (2,3) can execute a rolling-off and sliding movement, wherein the tibia plateau part (5) is pivotably mounted on the tibia shank part by a rotation mechanism, wherein a negative and positive fit between the femoral part (1) and the tibia plateau part (5) is produced up to a predetermined bending angle of the knee joint, such that a rotational movement of the femoral part (1) on the tibia shank part can be executed due to the pivotable mounting of the tibia plateau part (5) on the tibia shank part, and wherein the femoral part (1) is enabled to execute an increasing rotation of the femoral part (1) relative to the tibia plateau part (5) as the bending of the knee joint increases starting from the predetermined bending angle, without activating the rotation mechanism between the tibia plateau part (5) and the tibia shank part.

2. The knee joint endoprosthesis according to claim 1, wherein the predetermined bending angle lies in a range of about 20° to 40°, and wherein the negative and positive fit between the femoral part (1) and the tibia plateau part (5) is produced up to a point at which this angle is exceeded.

3. The knee joint endoprosthesis according to claim 1, wherein a ventrally situated web (9) transitions continuously into a dorsally-situated web (8).

4. The knee joint endoprosthesis according to claim 1, wherein the rotation mechanism between the tibia plateau part (5) and the tibia shank part has a pin integrally formed on the shank part and pointing toward the femur and has a correspondingly dimensioned bore in an underside of the tibia plateau part (5) in which the pin engages.

5. The knee joint endoprosthesis according to claim 1, wherein the runners (2, 3) delimit between them an open space (4) running from ventral toward dorsal, wherein the two slide guides (6) are separated by two webs (8, 9) oriented to run from dorsal toward ventral, wherein the dorsally-situated web (8) has a height such that, up to the predetermined bending angle of the knee joint, the web (8) engages in the open space (4) between the runners (2, 3) and thereby produces the negative and positive fit, and wherein the ventrally situated web (9) has only such a height that, as bending of the knee joint increases, an increasing rotation of the femoral part (1) relative to the tibia plateau part (5) is enabled.

6. The knee joint endoprosthesis according to claim 5, wherein the predetermined bending angle lies in a range of about 20° to 40°, and wherein the negative and positive fit between the femoral part (1) and the tibia plateau part (5) is produced up to a point at which this angle is exceeded.

7. The knee joint endoprosthesis according to claim 5, wherein the ventrally situated web (9) transitions continuously into the dorsally-situated web (8).

8. The knee joint endoprosthesis according to claim 5, wherein the rotation mechanism between the tibia plateau part (5) and the tibia shank part has a pin integrally formed on the shank part and pointing toward the femur and has a correspondingly dimensioned bore in an underside of the tibia plateau part (5) in which the pin engages.

* * * * *